(12) United States Patent
Khangaonkar et al.

(10) Patent No.: US 9,072,787 B2
(45) Date of Patent: Jul. 7, 2015

(54) EMULSIONS PROVIDING STABLE VITAMIN COMPOSITIONS AND METHODS OF FORMING COMPOSITIONS THEREOF

(71) Applicant: DR PEPPER/SEVEN UP, INC., Plano, TX (US)

(72) Inventors: Archana Khangaonkar, Plano, TX (US); Jeffrey D. Nutt, Plano, TX (US)

(73) Assignee: DR PEPPER/SEVEN UP, INC., Plano, TX (US)

( * ) Notice: Subject to any disclaimer, the term of this patent is extended or adjusted under 35 U.S.C. 154(b) by 0 days.

(21) Appl. No.: 14/452,072

(22) Filed: Aug. 5, 2014

(65) Prior Publication Data

US 2015/0004238 A1    Jan. 1, 2015

Related U.S. Application Data

(63) Continuation of application No. 13/931,493, filed on Jun. 28, 2013, now Pat. No. 8,828,457.

(51) Int. Cl.
| | |
|---|---|
| A01N 65/00 | (2009.01) |
| A61K 47/46 | (2006.01) |
| A61K 36/00 | (2006.01) |
| A23L 1/303 | (2006.01) |
| A61K 9/107 | (2006.01) |
| A61K 31/015 | (2006.01) |
| A61K 31/07 | (2006.01) |
| A61K 31/355 | (2006.01) |
| A23L 1/302 | (2006.01) |
| A23L 2/52 | (2006.01) |
| A23L 2/56 | (2006.01) |

(52) U.S. Cl.
CPC ............ *A61K 47/46* (2013.01); *A61K 36/00* (2013.01); *A23L 1/303* (2013.01); *A61K 9/107* (2013.01); *A61K 31/015* (2013.01); *A61K 31/07* (2013.01); *A61K 31/355* (2013.01); *A23L 1/302* (2013.01); *A23L 2/52* (2013.01); *A23L 2/56* (2013.01)

(58) Field of Classification Search
CPC .................................................. A61K 36/00
USPC ............................................... 424/725
See application file for complete search history.

(56) References Cited

U.S. PATENT DOCUMENTS

| | | | |
|---|---|---|---|
| 7,732,001 B2 | 6/2010 | Smorholm | |
| 8,153,180 B2 | 4/2012 | Grenville et al. | |
| 8,318,233 B2 | 11/2012 | Tran et al. | |
| 8,357,420 B2 | 1/2013 | Cox et al. | |

OTHER PUBLICATIONS

"Q-Naturale—Nature's high-efficiency emulsifier," http://foodinnovation.com/foodinnovation/en-us/Ingredients/Pages/Q-Naturale.aspx; printed Sep. 30, 2013, 2 pages.

*Primary Examiner* — Michael Meller
(74) *Attorney, Agent, or Firm* — Dykema Gossett P.L.L.C.

(57) ABSTRACT

Stable vitamin oil-in-water emulsions and methods of making those emulsions are described herein. The emulsions may be used to make beverage products that include fat-soluble vitamins. The emulsions may also be used in beverage products that are colored and which maintain color stability for an extended period of time.

5 Claims, 3 Drawing Sheets

EMULSIONS PROVIDING STABLE VITAMIN COMPOSITIONS AND METHODS OF FORMING COMPOSITIONS THEREOF

CROSS REFERENCE TO RELATED APPLICATIONS

This application is a continuation of U.S. patent application Ser. No. 13/931,493 filed on Jun. 28, 2013, the disclosure of which is hereby incorporated by reference in its entirety.

FIELD

The present application relates to emulsions that include fat-soluble vitamins suitable for use in a variety of consumable items and to methods of producing such emulsions.

BACKGROUND

Among vitamins that are important for proper nutrition are fat-soluble vitamins, a group that includes vitamins A, D, E, and K. A vitamin may include any of a number of related compounds that may share structural and/or functional characteristics. For example, vitamin A includes a number of related and biologically active compounds such as retinol, retinoic acid, and retinal. Each of the aforementioned vitamin A compounds includes an unsaturated hydrocarbon-containing chain, and the compounds serve various roles in the body. For example, vitamin A compounds may be antioxidants and may decrease cellular damage that may otherwise occur from the presence of some reactive species that may be produced during metabolism.

In addition to chemical forms active in the body, a number of provitamin forms of vitamin A and other fat-soluble vitamins may be included in foods and beverages. Beta-carotene, for example, is a provitamin form of vitamin A that may be converted by enzymatic processes to retinol in the liver. Therefore, beta carotene may be an effective source of retinol if consumed, and beta carotene may be substituted for vitamin A in food and beverage formulations.

As well as serving as a source of vitamin A, beta-carotene may function as a pigment and strongly absorbs light in blue-green regions of the visible spectrum, a property that may be used to impart a deep reddish-orange or yellow coloration to food and beverage products. While beta-carotene possesses some desirable color properties, beta-carotene is not entirely stabile, and degradation of beta-carotene, which may be driven by either or both of heat and light, may limit the color stability of products incorporating beta-carotene. The limited photostability of beta-carotene, a characteristic shared by some other fat-soluble vitamins, may be associated with functional roles that make fat-soluble vitamins useful in the body. For example, the fat-soluble vitamins include species that may protect lipids from breakdown during metabolism; therefore, the ability of vitamins to interact with and potentially deactivate high energy intermediates, such as radicals and/or singlet oxygen, which may form from lipids or be present during lipid metabolism, may be a useful property. However, the capability of vitamins to interact with those intermediates may also facilitate undesirable reactions, such as oxidative decomposition, that may limit vitamin stability.

The aforementioned characteristics of vitamins and fats may pose challenges when incorporating fat-soluble vitamins in food and beverage formulations. For example, when used in those compositions, beta-carotene and/or other fat-soluble vitamins may be dispersed throughout the composition as an emulsion. However, when a vitamin is incorporated in the oil phase of an emulsion, a vitamin may be exposed to an environment that includes a surrounding concentration of lipids or fats, species that, as noted above, may break down to intermediate compounds that are capable of interacting with vitamins. In addition, in some consumable items, such as when a vitamin component is used to impart color to a food or beverage product, a vitamin may also be exposed to light which may further subject vitamin formulations to photochemical processes that may promote vitamin degradation. Therefore, use of fat-soluble vitamins in food and beverage formulations may commonly expose the vitamins to a number of conditions that limit their stability. There is a need for emulsions and consumable products including emulsions that impart color stability and/or minimize loss of vitamin activity in consumable compositions.

SUMMARY

In some embodiments, an oil-in-water emulsion may include an oil phase wherein the primary oil among all oils in said oil phase is limonene. The oil phase of an emulsion may, in some embodiments, further include additional oils such as oils that may be useful in storage and/or handling of vitamins as microparticulate suspensions. In some embodiments, in addition to limonene, up to about 40% additional oils may be incorporated into an emulsion. In some embodiments, a vitamin incorporated within an emulsion may be beta-carotene in an amount between about 1% and about 5% by weight, and the emulsion may further include a surfactant portion of a quillaja extract in an amount between about 2.5% to about 20% by weight.

In some embodiments, a method of making an emulsion or beverage product may include addition of at least one fat-soluble vitamin to a suitable solvent oil, controlled thermal processing to aid in dissolving and/or mixing of the vitamin and solvent oil, addition of an emulsion stabilizer, and high pressure homogenization

DETAILED DESCRIPTION

Figure 1:
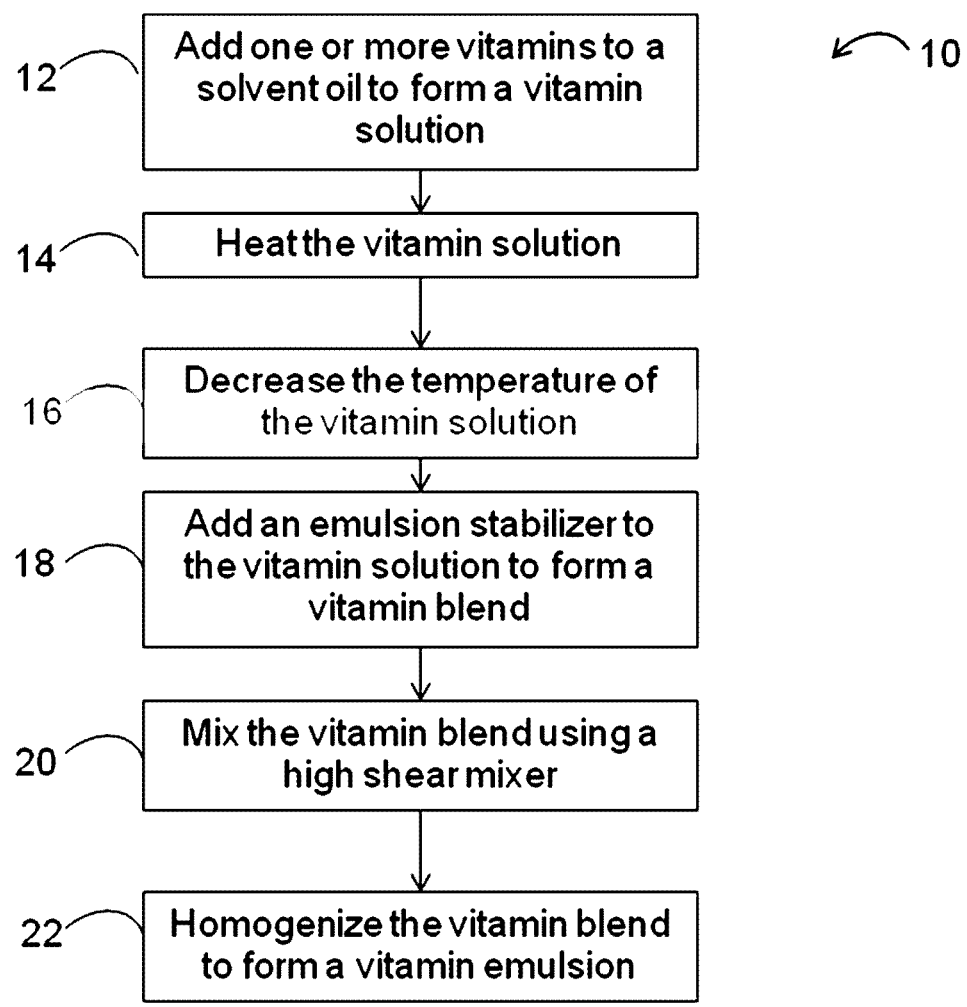
FIG. 1 is a flowchart showing a method of making an emulsion.

The following terms as used herein should be understood to have the indicated meanings.

When an item is introduced by "a" or "an," it should be understood to mean one or more of that item.

The term "beverage" means any drinkable liquid or semi-liquid, including for example flavored water, soft drinks, fruit drinks, slush products, smoothies, coffee-based drinks, tea-based drinks, juice-based drinks, milk-based drinks, dairy compositions, gel drinks, soy-based drinks, protein drinks, carbonated or non-carbonated drinks, alcoholic or non-alcoholic drinks.

The term "carrier oil" means an oil in which a fat-soluble vitamin may be stored as a stable suspension.

The term "comprises" means includes but is not limited to.

The term "comprising" means including but not limited to.

The term "consumable item" means anything that may be orally ingested by a consumer, including without limitation a food, beverage, pharmaceutical composition, nutraceutical composition, vitamin, lozenge, dietary supplement, confection, chewing gum, candy, and a combination of any of the foregoing.

The term "having" means including but not limited to.

The term "ppm" means parts per million by weight.

The term "primary component" when specified with respect to a composition or part of a composition refers to the component that is the most prevalent by mass of all components in the composition or composition part.

The term "provitamin" means a vitamin precursor that may be converted within the body to an active vitamin form.

The term "suspension" means a mixture that includes solid matter that is not dissolved.

The term "vitamin" means a composition including any combination of one or more related compounds commonly associated with a given vitamin form. A vitamin may include any combination of biologically active compounds, provitamin compounds, and/or intermediate compounds (such as may be used in storage and/or delivery) of a vitamin compound.

The term "vitamin A" means a composition including one or more of retinol, retinal, retinoic acid, any other form of vitamin A active in the body, provitamin form of any of the foregoing, intermediate form of any of the foregoing, ester of any of the foregoing, or any combination thereof. By way of nonlimiting example, provitamin and/or intermediate forms of vitamin A may include any of various carotenoids such as β-carotene, α-carotene and γ-carotene. By way of nonlimiting example, ester forms of vitamin A may include retinyl acetate or retinyl palmitate.

The term "weighting agent" means a composition that may be added to increase the density of an oil phase in an oil-in-water emulsion. By way of nonlimiting example, weighting agents may include brominated vegetable oil (BVO), sucrose acetate isobutyrate (SAIB), ester gums, glycerol ester of wood rosin, and combinations thereof.

This disclosure is directed to oil-in-water emulsions that include fat-soluble vitamins, beverages that include oil-in-water emulsions, and methods of producing the aforementioned beverages and/or emulsions. The emulsions and beverages described herein may include any of a number of vitamins, including water-soluble vitamins, but the compositions are particularly amenable for use with fat-soluble vitamins, including those that may be susceptible to thermal and/or photochemical decomposition. A method of preparing an oil-in-water emulsion may, in some embodiments, include addition of at least one fat-soluble vitamin to a suitable solvent, controlled thermal processing to aid in dissolving and/or mixing, addition of an emulsion stabilizer, and high pressure homogenization.

The emulsions described herein may be added to any beverage, beverage intermediate, or beverage concentrate in which an emulsion may be suitably added including by way of nonlimiting example carbonated or non-carbonated soft drinks, dairy compositions, protein-fortified beverages, cocktails, and juices. An emulsion may be diluted as desired for a beverage product. For example, an emulsion may be diluted in water and/or other ingredients to form a beverage product that is itself an emulsion, and in some embodiments, the added emulsion may comprise only a small fraction of the beverage product. An emulsion may, in some embodiments, be highly concentrated and may include a high oil-to-water ratio. The addition of a concentrated emulsion to other beverage components may be advantageous for a number of reasons. For example, an emulsion may be conveniently added to various beverages or beverage intermediates without significant dilution and/or significant adjustment of the concentrations of other ingredients in any composition to which it is added. In addition, it may be desirable to create concentrated beverage emulsions because doing so may enable the production of beverage products that are emulsions without requiring that large volumes of material be processed in the capital equipment used in making the emulsion. In addition, some ingredients of beverages may not be suitable for a homogenization protocol, and addition of a concentrated emulsion may enable those ingredients to be conveniently incorporated in beverage products that are emulsions. However, in some embodiments, a beverage may be prepared by addition of ingredients prior to formation of an emulsion and then processed to form the emulsion.

In some embodiments, an emulsion may include only a small amount of added water and may include a high oil-to-water ratio. In some embodiments, an emulsion may include no more than about 25% water, no more than about 50% water, or no more than about 80% water by weight.

In some embodiments, including but not limited to those embodiments of emulsions that may provide color stability to a beverage, an emulsion may be added to a beverage at about 0.02% to about 0.12% or about 0.05% to about 0.09% by weight. In some embodiments, an emulsion may include beta-carotene at weight percentages of between about 1% to about 5%, about 2% to about 4%, or about 2.8% to about 3.2%. An emulsion including a weight percentage of beta-carotene within any of the aforementioned ranges may be added to a beverage in weight percentages described herein or another amount may be added to achieve an appropriate concentration in a beverage. Where reference is made to the concentration of a component in an emulsion, addition of the emulsion may provide that component to a beverage product as may be calculated for a given amount or weight percentage of the added emulsion. In some embodiments of beverages, beta-carotene may be included in amounts by weight of about 5 ppm to about 40 ppm, about 10 ppm to about 30 ppm, or about 20 ppm.

In some embodiments, a vitamin or combination of vitamins may be included in an emulsion, and appropriate concentrations of the vitamins in the emulsion and/or suitable amounts of the emulsion may be selected for addition to other components to form a desired beverage product. Appropriate concentrations and/or dilutions may, for example, be used such that a beverage serving includes a desired percentage of a recommended daily allowance of a vitamin.

Emulsions described herein have been found to be stable for a period of time of at least about 3 months to about 4 months. In some embodiments, concentrated emulsions of low-water content that include beta-carotene may be stored for a period of at least 4 months and may be added at any time during storage to other ingredients to form a beverage product that includes a desired color. In some embodiments, beverages made using the emulsions described herein have been found to be stable for at least about 4 months or at least about 6 months. In some embodiments, an emulsion or beverage product comprising an emulsion may be shelf stable and may meet a number of characteristics including by way of nonlimiting example physical stability of the emulsion, preservation of significant biological activity of included vitamins, maintenance of color intensity and/or purity, absence of biological degradation, or any combinations of the aforementioned characteristics. In some embodiments, an emulsion or beverage comprising an emulsion may be physically stable, and oil-phase regions of the emulsion may remain homogeneously dispersed within the continuous phase of the emulsion. Furthermore, for the compositions described herein, significant increase in the size of oil-phase particles, such as may be characterized by a noticeable increase in turbidity, has not been evident. In some embodiments, no significant decrease in color intensity and/or significant color shifts may occur during storage and/or handling of an emulsion or beverage comprising an emulsion. In some embodiments, desired flavors may be maintained and/or no undesirable off-notes may form during storage and/or handling of an emulsion or beverage comprising an emulsion. In addition, both emulsions and beverages described herein may be handled and/or stored as appropriate to maintain biological stability of the composition. For example, the emulsions may be stored without significant growth of bacteria, spores, or other contaminant species.

Emulsions described herein may include any of various fat-soluble vitamins including by way of nonlimiting example vitamins A, D, E, K, provitamin and/or intermediate forms thereof, and any combinations of the aforementioned. Particular benefits derived from the emulsions described herein are found for vitamin and provitamin forms that may be susceptible to oxidative degradation. Additionally, some embodiments described herein, such as for example embodiments that include antioxidant components (including components that may react with oxygen, hydroxyl, or peroxyl radicals) and/or singlet oxygen scavengers, may be particularly useful for emulsions designed to impart color stability to beverages. In some embodiments, a vitamin A carotenoid, such as beta-carotene, may be included in a beverage emulsion that comprises a dispersed phase that is an oil wherein the oil and/or one or more oil-soluble reagents are either or both of antioxidants and/or singlet oxygen scavengers. For example, in some embodiments, beta-carotene may be dissolved in limonene or dissolved in a mixture of limonene and other terpene compounds that may be antioxidants. In some embodiments, a solvent that possesses antioxidant activity may be used in combination with another antioxidant, such as a tocopherol compound, that may also be present within the oil phase of an emulsion.

In some embodiments, methods of making an oil-in-water emulsion may include a step of addition of one or more vitamins to a suitable solvent oil to form a vitamin solution. Solvents in which a fat-soluble vitamin (or combination of vitamins) may be added include solvents oils that are suitable for human consumption and in which the fat-soluble vitamin or combination of vitamins may be sufficiently soluble. Upon processing to form an emulsion, a solvent oil or part of the solvent oil may be part of a dispersed phase in the emulsion or part of a dispersed phase in a beverage product comprising the emulsion. Fat-soluble vitamins may become trapped or preferentially reside in the dispersed phase of the emulsion, and the emulsion may protect the vitamin from substantial exposure to a surrounding aqueous environment. In some embodiments, use of one or more oils or oils in combination with an emulsion stabilizer may substantially confine a vitamin to the dispersed phase of an emulsion, and confinement of the vitamin may provide an environment wherein thermal and/or photochemical degradation of the vitamin may be substantially inhibited. For example, oxidative reactions may be substantially less than if the vitamin were exposed to water or some lipid environments that include a substantial proportion of unsaturated fatty acids.

In some embodiments of methods of making an emulsion, a vitamin may be suspended or dissolved in an oil including by way of nonlimiting example vegetable oil, coconut oil, soybean oil, safflower oil, corn oil, sunflower oil, palm oil, canola oil, marine oil, cottonseed oil, medium-chain triglycerides, limonene, an oil derived from a citrus rind, and combinations thereof. In some embodiments, particles of a fat-soluble vitamin may be stored and/or handled as a suspension maintained in a carrier oil. Vitamin suspensions are commercially available from a number of sources. For example, an about 30% suspension of beta-carotene in sunflower oil is commercially available, and may be provided from DSM Food Specialties (Parsippany, N.J.) under the trade name CaroPure™. Other commercially available suspensions of beta-carotene include by way of nonlimiting example suspensions maintained in soybean oil, corn oil, and medium-chain triglycerides.

In some embodiments, fat-soluble vitamins may be stored and/or handled in the form of a solid, solid crystal, or carrier-oil suspension. For example, in some embodiments, a vitamin suspension in a carrier oil may be stored without significant loss of vitamin activity for at least a period of time, and the vitamin suspension may then be added to a solvent oil and dissolved therein in a process of making an emulsion. Upon processing, at least a portion of both the carrier and solvent oils may become components of the oil phase in a prepared oil-in-water emulsion.

A suspension of a fat-soluble vitamin may include microscopic crystals of a vitamin, and the vitamin suspension may therefore be microscopically heterogeneous. While microparticle suspensions may be convenient for storage, the use of microparticle suspensions may be challenging when integrating those suspensions in methods of making an emulsion. For example, in some solvents, microparticulate matter may only dissolve slowly. That characteristic may be an undesirable attribute for some commercial applications designed to be high in throughput. In addition, if particles of a vitamin are not dissolved or if particles reform after initial dissolution, particulate matter may be present during homogenization, and a portion of vitamin may not be properly incorporated within the oil phase of an emulsion. In such circumstances, inadvertent exposure of a fat-soluble vitamin to the aqueous phase of an emulsion and/or loss of vitamin activity may occur.

To avoid loss or degradation of a vitamin, it may be advantageous for a solvent oil to which the vitamin is added to efficiently penetrate and rapidly dissolve solid matter that may be present. Solvent oils comprising limonene have herein been found to facilitate rapid dissolution of solid portions of fat-soluble vitamins including solid portions that may be added in the form of microparticulate matter.

In some embodiments of methods of making an emulsion, heat may be used to facilitate dissolution of vitamin that may be present in solid form and/or present as microparticulate matter. For example, heat may be added to a solution during or after the addition of a vitamin. In some embodiments, application of heat and use of a solvent oil that includes limonene may facilitate dissolution and mixing at temperatures and times where a substantial number of particles may remain if other solvents and/or conditions were used. For example, when using medium-chain triglycerides as the primary portion of a solvent oil, the solvent may dissolve vitamin microparticles only at significantly higher temperatures and/or at longer time periods than if solvent oils including limonene are used. When using a primary portion of medium-chain triglycerides in a solvent oil, it is not known whether dissolution is difficult because the oil is hindered from contact with microparticles due to improper mixing with the carrier oil, whether the solvent only slowly interacts with the surface of solid particles, or whether other factors limit those solvent oils. However, none of those concerns are substantially limiting when using solvent oils or solvent oils in combination with carrier oils as described herein.

Following the addition of a vitamin to a solvent oil and heating the resulting vitamin solution, it may, in some embodiments, be desirable to decrease the temperature of the vitamin solution. Lowering the temperature of the vitamin solution may, for example, serve to minimize thermal degradation and/or minimize other undesirable changes in vitamin components, solvent components, and/or other ingredients that may be present in the vitamin solution. While beneficial for the aforementioned reasons, in other methods, for example methods that use other solvents and/or other method conditions, formation of particulate matter when decreasing the temperature of a vitamin solution may be problematic. The creation of particulate matter upon decreasing the temperature of a vitamin solution may be particularly problematic when significant amounts of some oils, including some that may be used as carrier oils, are present in the vitamin solution. In some embodiments, solvent oils that include limonene may be particularly useful to minimize formation of vitamin particles when decreasing the temperature of a vitamin solution. In some embodiments of methods of making a vitamin oil-in-water emulsion, a vitamin solution may include a primary component of limonene and may comprise up to about 25% or up to about 40% of other oils. By way of nonlimiting example other oils may include soybean oil, corn oil, medium-chain triglycerides, sunflower oil, a carrier oil, one or more other component oils, or combinations thereof. In some embodiments, a beverage emulsion may include an oil phase wherein the primary oil among all oils in said oil phase is limonene, and up to about 25% or up to about 40% of all oils in the oil phase may be other oils.

In some embodiments, beta-carotene may be stored and handled in the form of a carrier-oil suspension wherein the carrier oil may be corn oil, and the suspension may be added to limonene solvent oil or to a solvent oil derived from a citrus rind. In some embodiments, an about 30% by weight suspension of beta-carotene in corn oil (or some other suitable percentage by weight of beta-carotene) may be added to a solvent oil that includes a primary component of limonene or may be added to a solvent oil derived from a citrus rind and comprising a primary portion of limonene. In addition, the solvent oil may be the majority component of all oils added to form a vitamin solution, and the primary component of all oils in a solvent oil or vitamin solution may also be the primary portion of all oils in a finally prepared emulsion.

In some embodiments, the overall severity of conditions for making an emulsion (temperature and time of heating) may be low. In some embodiments, a method of making an emulsion may include a maximum process temperature of about 140° C. In some embodiments, a target temperature or temperature range may be applied for a time period of no longer than about 10 minutes. In some embodiments of making an emulsion, following heating to a maximum process temperature, the temperature may be lowered and maintained at less than about 100° C. during additional remaining steps in a process of making an emulsion.

In contrast to the reagents, temperatures, and/or times described in embodiments herein, if other more severe reagents, temperature, and/or heating times during processing are used, thermal damage to components of an emulsion may occur. For example, unacceptable levels of even small amounts of undesired products, such as peroxides, may form or be present. While initially such compositions may appear intact, the presence of small amounts of those undesired products may have an effect on product stability and lifetime. For example, for some beverages, such as those that include beta-carotene for providing color, processing under unacceptable thermal conditions may result in the production of peroxide or other defects, and those defects may influence the resultant color stability of the beverage. In addition, for some beverages, such as those that include limonene and/or other citrus flavors, small amounts of breakdown products formed during production of an emulsion may influence the formation of undesirable off-notes which may also limit the lifetime of beverage products that include those emulsions. Therefore, for some beverages, loss of color stability, loss of beverage flavor, the production of off-notes, or other factors may limit product lifetime.

In some embodiments of methods of making an emulsion, one or more processing steps may be performed under conditions wherein the amounts of ambient or dissolved oxygen present may be decreased. For example, in some embodiments, it may be desirable to form an oil-in-water emulsion under conditions in which at least some proportion of ambient or dissolved oxygen is displaced by another gas. Such embodiments may, for example, be useful when incorporating labile flavoring components to a beverage, such as some terpene compounds, adding some amounts of pro-oxidative species to a beverage, such as certain metals, or when incorporating other compounds that may be susceptible to oxidation. However, the beverages described herein and/or made using methods herein have been found to be stable without decreasing levels of oxygen below those typically found in carbonated or non-carbonated beverages.

In some embodiments, limonene or other citrus extract compounds may be used to impart one or more fragrances and/or flavors to a beverage that includes an oil-in-water emulsion. Various citrus fruits may, in some embodiments, be used as a source of limonene or other components of a citrus rind. For example, limonene may be derived from citrus fruits classified as hesperidia including but not limited to oranges, lemons, limes, mandarins, and grapefruits, and may be the primary compound in oils extracted therefrom. Limonene may, in some embodiments, be obtained during operations in the production of fruit juice. For example, as a fruit is pressed or pulverized, oils typically concentrated in the peels or other structural components of the fruit may be released. The oils may be separated from other components using standard methods such as by subjecting the pressed composition to cycles of evaporation and condensation.

Any of various citrus fruits may be used to extract limonene; however, extracts from some citrus rinds may also contain a minority portion of other compounds including by way of nonlimiting example a number of terpene and/or terpenoid compounds. Some of the compounds found in citrus rind extracts may include cyclic and acyclic monoterpenes, as well as some amount of higher-order terpene and/or terpenoid compounds. Some of those compounds may include oxygen (which may for example be present as a hydroxyl, carboxyl, ketone, or aldehyde functionality), and the inclusion of oxygen may generally decrease the stability of those compounds. For some terpenes and/or terpenoids, stability may be characterized as a susceptibility to photochemical and/or autooxidative processes, and those processes may be associated with the production of radical species that may negatively interact with some fat-soluble vitamins such as beta-carotene. Therefore, for some embodiments of emulsions and beverages including emulsions, it may be desirable to minimize the concentrations of minor components that may be derived from a citrus rind, such as oxygen including species that may be chemically reactive.

In some embodiments, a citrus rind extract oil may be processed in order to purify the oil to include limonene at a level of greater than about 95%, about 98%, or about 99% purity by weight. In some embodiments, a fruit rind extract may include less than about 5% of terpene components other than limonene. The concentration of minor components in a citrus rind extract may be reduced using various processes. In some embodiments, purification of limonene to a desired level may be achieved using steam extraction and/or any combination of steam extraction, steam distillation, and vacuum distillation.

In some embodiments, an oil from a citrus rind may be processed using the aforementioned techniques or additional methods to remove a minor component of the oil that may be prone to oxidative and/or photooxidative processes. By way of nonlimiting example, minor components of a citrus rind extract that may be removed during purification of limonene may include mycrene, citronellal, and citral. In some embodiments, the removal of one or more minor components of a citrus rind extract may include addition of a reagent designed to bind and/or trap the one or more minor components, and the bound reagent and component may then be selectively removed.

In some embodiments, an oil-in-water emulsion may incorporate a reagent that improves the stability of the emulsion. Reagents that improve the stability of oil-in-water emulsions may, for example, be emulsifiers and may be referred to herein as "stabilizing agents" or "stabilizers." Representative stabilizing agents used in beverages may include, for example, yucca schidigera extracts, quillaja extracts, Labiatae herb extracts, carnosic acid, esters of carnosic acid (including methyl carnosate and ethyl carnosate), carnosol, rosmariquinone, rosmanol, epi-rosmanol, isorosmanol, rosmaridiphenol, 12-methoxycaniosic acid, *Sophora japonica* saponin, enzyme-treated lecithins, enzyme-digested lecithins, plant sterols, plant lecithins, sphingolipids, soybean saponin, bile powder, animal sterols, tomato glucolipids, fractionated lecithins, barley husk extract, enzyme-treated soybean saponin extract, tea seed saponin, beet saponin, propylene glycol fatty acid esters, sarsaparilla extracts, sorbitan fatty acid esters, sucrose fatty acid esters, and mixtures thereof. In some embodiments, a stabilizer may comprise or consist of quillaja extracts.

Quillaja extracts have been found to be particularly amenable for achieving stable oil-in-water emulsions as described herein. In some embodiments, a stabilizing agent comprising or consisting of quillaja extract may be used in an oil-in-water emulsion including limonene and beta-carotene. For example, such embodiments have been found to be useful in beverages wherein the emulsion is not only physically stable but also maintains color stability. In some embodiments, emulsions including limonene and quillaja extract may be stable over a range of pH values of about 3.0 to about 3.5, about 3.0 to about 5.0, or about 3.0 to about 8.0. Moreover, such compositions have advantageously been found to be stable even in the absence of weighting agents that are commonly used to improve the stability of beverage emulsions. In some embodiments, an emulsion or beverage comprising an emulsion may be both physically stable and provide color stability even in the absence of weighting agents. Some of the plant extracts described herein are commercially available. For example, quillaja extract can be obtained from Ingredion Inc. (Westchester, Ill.) under the trade name Q-Naturale™ (hereafter, "Q-Naturale").

In some embodiments, an emulsion may include an emulsion stabilizer that comprises Q-Naturale, and the emulsion may also include up to about 50% by weight of a solvent oil comprising limonene or a primary portion of limonene. Within that range, the solvent oil may, in some embodiments, be included in the emulsion in weight percentages of at least about 15%, about 25%, or about 30%. Also within that range, the solvent oil may, in some embodiments, be included in the emulsion in weight percentages of at most about 45% or about 35%. The solvent oil may, in some embodiments, be included in the emulsion in weight percentages of about 15% to about 50%, or about 25% to about 45%, or about 30% to about 35%. Q-Naturale may, in some embodiments, be included in the emulsion in amounts of about 35% to about 65% by weight, or about 50% to about 60% by weight. In some embodiments, an emulsion may be preparing as concentrated emulsions and may include only a small amount of added water. Addition of a concentrated emulsion may be useful in preparing a beverage suitable for consumption. In some embodiments, Q-Naturale may be present in a prepared beverage in amounts of about 100 ppm to about 700 ppm or about 200 ppm to about 500 ppm.

A quillaja extract may include a portion of water or added water and also include a portion of active components. For example, a quillaja extract may comprise an active portion of surfactants the majority of which may comprise saponins. An active portion of a quillaja extract may herein be referred to as a surfactant portion of the extract.

In some embodiments, an emulsion may include quillaja extract, and the emulsion may also include a solvent oil comprising limonene. For example, a surfactant portion of a quillaja extract may be included in an emulsion in an amount of about 2.5% to about 20% by weight. A surfactant portion of a quillaja extract may, in some embodiments, be included in an emulsion in weight percentages of at least about 3.5%, about 5.0%, or about 6.5%. Also within the above range, a surfactant portion of the quillaja extract may, in some embodiments, be included in an emulsion in weight percentages of at most about 18%, about 15%, or about 12%. A solvent oil may comprise a primary portion of limonene and may, in some embodiments, be included in the emulsion in amounts of about 15% to about 50% by weight. Within that range, a solvent oil may, in some embodiments, be included in an emulsion in weight percentages of at least about 20%, about 25%, or about 30%. Furthermore, within that range, a solvent oil may, in some embodiments, be included in an emulsion in weight percentages of at most about 45%, about 40%, or about 35%. In some embodiments, a ratio of oils to a surfactant portion of a quillaja extract by weight may be about 8:1 to about 2.5:1, or about 5:1 to about 3:1 in a prepared oil-in-water emulsion.

As described previously, an emulsion may be added to other ingredients and diluted to form a beverage product. In some embodiments, a surfactant portion of a quillaja extract may be present in a prepared beverage in amounts of about 20 ppm to about 140 ppm or about 40 ppm to about 100 ppm.

In some embodiments, an emulsion may include a solvent oil wherein the solvent oil comprises an oil derived from a citrus rind. Included among terpenes and/or terpenoids that may be commonly present in a citrus rind extract are some that may, to varying degrees, be prone to instability and which may, under some conditions, form peroxides and/or other breakdown products. For example, limonene is a terpene that may exhibit better stability than some diterpenes and diterpenoid compounds that may include oxygen. In some embodiments, a citrus rind extract may be selected or processed to include a minimal concentration of peroxide compounds. In some embodiments, a citrus rind extract may be processed to remove a component terpene or terpenoid of the extract that may be prone to oxidation and/or photooxidative processes. Therefore, an oil derived from a citrus rind may, in some embodiments, be selected or processed to be low in peroxides and/or to be resistant to the formation of peroxides during the lifetime of an emulsion or beverage product that incorporates the extract. In addition, some components of a citrus rind extract may, to various degrees, also act as antioxidants. For example, limonene may, under some conditions, function as an antioxidant, and this activity may, at least in part, improve the stability of a fat-soluble vitamin included in an emulsion comprising limonene. Therefore, in some embodiments, a citrus rind extract may be processed to be resistant to the formation of peroxides and also include a purity level of limonene that improves the antioxidant activity of the extract.

In some embodiments, an oil component may be incorporated in an emulsion to decrease the susceptibility of the emulsion to the formation of peroxides and/or to increase the antioxidant activity of the oil phase of the emulsion. For example, in some embodiments, the oils in an emulsion may comprise a primary portion of limonene and other oils including by way of nonlimiting example other components of a citrus rind extract, carrier oils, one or more other component oils, or combinations thereof. The other component oils may, in some embodiments, be oils that are resistant to oxidation and/or the formation of peroxides. For example, the other component oils may, in some embodiments, include fatty acids that comprise or consist of saturated fatty acids or comprise or consist of saturated and monounsaturated fatty acids. In some embodiments, the other component oils may include a portion of fatty acid chains that are substantially free of polyunsaturated chains. In some embodiments, the oils in a vitamin solution may include up to about 10% of other oil components that comprise or consist of saturated fatty acids or comprise or consist of saturated and monounsaturated fatty acids. In some embodiments, oil components included among all oils in the oil phase of an oil-in-water emulsion may include up to about 10% of other component oils that comprise or consist of saturated fatty acids or comprise or consist of saturated and monounsaturated fatty acids.

In some embodiments, an emulsion may additionally include one or more antioxidants and/or singlet oxygen scavengers that may be soluble in the solvent oil. For example, in some embodiments, an emulsion may include a tocopherol antioxidant, tocotrienol antioxidant or a combination of both. Tocopherols may include any of various organic compounds that possess vitamin E activity in the body. Vitamin E may exist in a number of different forms including by way of nonlimiting example alpha-tocopherol, beta-tocopherol, gamma-tocopherol, delta-tocopherol, and several tocotrienols. The aforementioned vitamin E compounds possess antioxidant activity, and any combination of the aforementioned vitamin E forms may, in some embodiments, be added to the emulsions described herein. In some embodiments, vitamin E may be added to an emulsion in an amount of between about 0.1% to about 5%, or about 0.5% to about 2.0% by weight. In some embodiments, vitamin E may be present in a prepared beverage in amounts of about 0.2 ppm to about 25 ppm.

An embodiment of a method 10 for preparing a stable emulsion is shown in FIG. 1. In a step 12, one or more fat-soluble vitamins may be added to a solvent oil to form a vitamin solution. For example, in some embodiments, beta-carotene may be added to a solvent oil wherein limonene is the primary component of the solvent oil. In some embodiments, additional vitamins, other component oils, other components, or combinations thereof may also be added to the solvent oil, a carrier oil or to the vitamin solution.

In some embodiments, the one or more fat-soluble vitamins may be added to the solvent oil as a suspension of microparticles in a carrier oil. A carrier oil may include suspended particles of vitamin in any suitable amount. For example, an amount of carrier oil and vitamin particles may be used wherein the suspension may be conveniently stored without degrading. In some embodiments, an amount of carrier oil may be added to a solvent oil such that the carrier oil may be present in the resultant vitamin solution at up to about 30% by weight. In some embodiments, an amount of carrier oil may be added to the solvent such that the carrier oil may be present in the vitamin solution at about 10% to about 30% or about 20% to about 28% by weight.

In a step 14, the vitamin solution may be heated. As discussed above, heating may be desired to facilitate mixing of the solvent and carrier oils and/or penetration and dissolution of solid portions of an added one or more fat-soluble vitamins. In some embodiments, the vitamin solution may be actively stirred or mixed to further facilitate dissolution of solid matter. In some embodiments, the vitamin solution may be heated to a temperature of about 100° C. to about 140° C. Within that range, in some embodiments, a vitamin solution may be heated to a temperature that does not exceed about 135° C., about 130° C., or about 125° C. In some embodiments, the vitamin solution may be heated to a temperature of about 125° C. to about 130° C. or to a temperature of about 127° C. In some embodiments, the temperature may be held at about the target temperature or temperature range for about 5 minutes to about 10 minutes or for some other suitable period of time.

In some embodiments, a vitamin solution may be held at or near the target temperature or temperature range for a period of time that is predetermined. However, in some embodiments, the duration of heating may not be preset. For example, a time period for heating may be based on a measurement of whether added particulate matter remains present in the vitamin solution. For example, in some embodiments, a sample of a vitamin solution may be analyzed by light microscopy to determine that the solution is substantially free of crystalline matter. In some embodiments, a determination that vitamin particles are substantially dissolved may be based on a measurement of solution turbidity, a measurement of absorbance, another basis, or combinations of measurements thereof.

In a step 16, the temperature of the vitamin solution may be decreased. For example, in some embodiments, the temperature of the vitamin solution may be lowered to be within a temperature range of about 90° C. to about 110° C., about 80° C. to about 100° C., or about 70° C. to about 90° C. In some embodiments, the temperature of the solution may be lowered to a temperature of less than about 110° C., less than about 100° C. or less than about 90° C. The vitamin solution may, in some embodiments, be actively cooled while the solution is held for example in a chamber of a convenient size or the vitamin solution may be cooled by directing the solution to flow past a dedicated cooler located at some point on a solution flow line.

In some embodiments, the temperature established upon decreasing the temperature in a step 16 may be maintained until the emulsion is finally prepared. For example, it may be desirable to maintain the lowered temperature to minimize degradation of components in the composition or prevent other undesirable thermal effects. In some embodiments, following the cooling to a target temperature or temperature range, a temperature of about the target range may be maintained until the emulsion is formed. For example, a minimum temperature may be maintained to prevent any particulate matter from forming in the vitamin solution before the final product emulsion is produced.

In some embodiments, an appropriate amount of a liquid material maintained at a lower temperature than the solution may be added to the solution to promote cooling. For example, in the method 10 cooling of the vitamin solution is described as a separate step from the addition of an emulsion stabilizer, and in some embodiments, cooling of the solution may be executed before addition of the emulsion stabilizer. However, in some embodiments, addition of the emulsion stabilizer and cooling of the combination of a vitamin solution may be achieved concurrently or at least in part those steps may overlap in time. For example, the stabilizer or a solution including the stabilizer may be held at an appropriate temperate such as about 70° C. to about 90° C. or some other suitable temperature, and addition of the solution may facilitate cooling of the vitamin solution to which it is added.

In a step 18, an emulsion stabilizer may be added to the vitamin solution to form a vitamin blend. In some embodiments, the emulsion stabilizer may be a solution of Q-Naturale and may be added in an amount such that the vitamin blend or the prepared oil-in-water emulsion includes about 35% to about 65% by weight, or about 50% to about 60% by weight Q-Naturale. In some embodiments, the emulsion stabilizer may comprise quillaja extract or a diluted quillaja extract. For example, a quillaja extract or diluted quillaja extract may be added in an amount such that the vitamin blend or prepared oil-in-water emulsion includes a surfactant portion of about 2.5% to about 20% by weight.

In a step 20, a vitamin blend obtained upon addition of the emulsion stabilizer may be further processed to enhance mixing. For example, the vitamin blend may be processed using a high-shear mixer. Mixing may be executed for an appropriate period of time and at a desired temperature to ensure a desired level of mixing prior to homogenization. However, in some embodiments, sufficient mixing may be achieved after addition of the stabilizing agent, and the use of a high-shear mixer may be optional. Therefore, step 20 may be an optional step.

In a step 22, a vitamin blend may be subjected to high-pressure homogenization. Homogenization may include forcing the vitamin blend through a small orifice or opening under conditions of high pressure and/or high temperature. In some embodiments, homogenization may include subjecting the vitamin blend to a pressure in pounds per square inch of about 5,000 psi to about 7,000 psi, or about 6,000 psi to about 10,000 psi. In some embodiments, a two-stage homogenizer may be used, and the second stage of the homogenizer may apply a pressure that is significantly lower than the first stage pressure. In some embodiments, a pressure may be applied that is suitable to achieve oil-phase particles of an average size of about 0.10 microns to about 0.50 microns, about 0.10 microns to about 0.20 microns, or about 0.10 to about 0.15 microns. In some embodiments, a vitamin blend may be subjected to one or more passes through a high-pressure homogenizer. For example, in some embodiments, a vitamin blend may be passed through a two-stage homogenizer for two or more passes.

In some embodiments, the size of oil-phase particles of a homogenized or partially homogenized vitamin blend may be measured after passage through a homogenizer. For example, verification of the size of oil-phase regions may be made after either or both of a first pass and second pass through a high-pressure homogenizer. In some embodiments, a homogenized or partially homogenized vitamin blend that has been subject to a first pass through a homogenizer may only be processed through another pass if a desired particle size has not yet been achieved.

Figure 2:
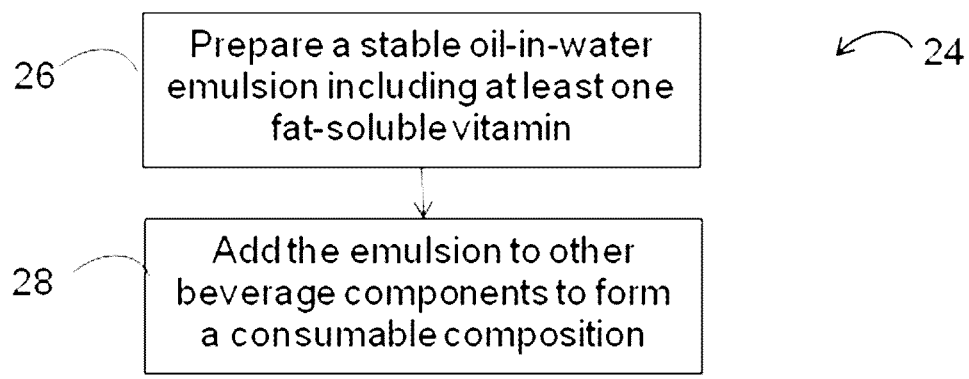
FIG. 2 is a flowchart showing a method of making a consumable composition.

An embodiment of a method 24 for preparing a beverage product that includes an oil-in-water emulsion is shown in FIG. 2. In a step 26 a stable oil-in-water emulsion including at least one fat-soluble vitamin may be prepared. For example, in some embodiments, the emulsion may be prepared as described with respect to a method 10. Emulsions prepared using the methods described herein may be stable and may be conveniently stored for a suitable period of time prior to further processing. In a step 28 the emulsion may be added to other beverage components to form a consumable composition.

In some embodiments, a consumable composition may include additives such as caffeine, coloring agents ("colorants," "colorings"), emulsifiers, food-grade acids, minerals, micronutrients, plant extracts, preservatives, salts (including buffering salts), stabilizers, thickening agents, medicaments, and a combination comprising any of the foregoing. Those of ordinary skill in the art will understand that certain additives may meet the definition or function according to more than one of the above-listed additive categories.

Exemplary salts may include alkali or alkaline earth metal chlorides, glutamates, and the like. For example, monosodium glutamate, potassium chloride, sodium chloride, and a combination comprising any of the foregoing salts may be used. The salts may be added to the beverage as a flavor potentiator as described above. Food-grade acids for use in certain embodiments of the consumable composition may include, for example, acetic acid, adipic acid, ascorbic acid, butyric acid, citric acid, formic acid, fumaric acid, glyconic acid, lactic acid, malic acid, phosphoric acid, oxalic acid, succinic acid, tartaric acid, and a combination comprising any of the foregoing food-grade acids. The food-grade acid may be added as acidulant to control the pH of the consumable composition and also to provide some preservative properties; or to stabilize the consumable composition. The pH of a beverage, syrup or mix, or concentrate may also be modified by the addition of food-grade compounds such as ammonium hydroxide, sodium carbonate, potassium carbonate, sodium bicarbonate, and the like, and a combination comprising any of the foregoing. Additionally, the pH may be adjusted by the addition of carbon dioxide. The pH may also affect the relative partition of solutes between liquid and solid portions of a beverage; such is particularly true if the pH is changed over a region where a solute becomes at least fractionally ionized. In some embodiments, the ionization of a component may be modified by selection of a pH that alters the fraction of a component which is ionized. In addition, a sweetener or bulk solute may in some cases be selected because within a desired pH range for a beverage, the component may exist in an ionized form.

A person having ordinary skill in the art will understand that embodiments of beverages may contain one or more flavors. Exemplary flavor oils may include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil; useful flavoring agents may include artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, prune, raisin, cola, guarana, neroli, pineapple, apricot, banana, melon, apricot, ume, cherry, raspberry, blackberry, tropical fruit, mango, mangosteen, pomegranate, papaya and so forth. Additional exemplary flavors imparted by a flavoring agent may include a milk flavor, a butter flavor, a cheese flavor, a cream flavor, and a yogurt flavor; a vanilla flavor; tea or coffee flavors, such as a green tea flavor, an oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamon flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; a nut flavor such as an almond flavor, a hazelnut flavor, a macadamia nut flavor, a peanut flavor, a pecan flavor, a pistachio flavor, and a walnut flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor.

In some embodiments, other flavoring agents may include aldehydes and esters such as cinnamyl acetate, cinnamaldehyde, citral diethylacetal, dihydrocarvyl acetate, eugenyl formate, p methylamisol, and so forth. Examples of aldehyde flavorings may include acetaldehyde (apple), benzaldehyde (cherry, almond), anisic aldehyde (licorice, anise), cinnamic aldehyde (cinnamon), citral, i.e., alpha citral (lemon, lime), neral, i.e., beta citral (lemon, lime), decanal (orange, lemon), ethyl vanillin (vanilla, cream), heliotrope, i.e., piperonal (vanilla, cream), vanillin (vanilla, cream), alpha amyl cinnamaldehyde (spicy fruity flavors), butyraldehyde (butter, cheese), valeraldehyde (butter, cheese), citronellal (modifies, many types), decanal (citrus fruits), aldehyde C 8 (citrus fruits), aldehyde C 9 (citrus fruits), aldehyde C 12 (citrus fruits), 2 ethyl butyraldehyde (berry fruits), hexenal, i.e., trans 2 (berry fruits), tolyl aldehyde (cherry, almond), veratraldehyde (vanilla), 2,6 dimethyl 5 heptenal, i.e., melonal (melon), 2,6 dimethyloctanal (green fruit), and 2 dodecenal (citrus, mandarin), and the like.

The flavoring agents may be used in liquid or solid/dried form and may be used individually or in a mixture. When employed in dried form, suitable drying means such as spray drying an oil may be used. Alternatively, the flavoring agent may be absorbed onto water-soluble materials, such as cellulose, starch, sugar, maltodextrin, gum arabic and so forth or may be encapsulated. In still other embodiments, the flavoring agent may be adsorbed onto silicas, zeolites, and the like. The techniques for preparing such dried forms are well-known.

In some embodiments, the flavoring agents may be used in many distinct physical forms. Without being limited thereto, such physical forms may include free forms, such as spray dried, powdered, beaded forms, encapsulated forms, emulsions such as caramel or gum arabic emulsions, and a combination comprising at least one of the foregoing physical forms. The particular amount of the flavoring agent effective for imparting flavor characteristics to the composition may depend upon several factors including the flavor, the flavor impression, and the like.

In some embodiments, the tartness of a beverage may be varied by selecting and combining acids to provide a desired tartness perception. Some factors to consider in determining a desired tartness include, for example, the acid's dissociation constant, solubility, pH, etc. These variables may be measured by measuring the titratable acidity of a beverage, syrup or mix, or concentrate.

In some embodiments, a coloring agent may be used in amounts effective to produce a desired color for the composition. Exemplary coloring agents may include pigments, natural food colors and dyes suitable for food, drug and cosmetic applications. A full recitation of all colorants approved by the United States Food and Drug Administration, together with corresponding chemical structures, may be found in the Kirk-Othmer Encyclopedia of Chemical Technology, 3rd Edition, in volume 5 at pages 857-884.

As classified by the United States Food, Drug, and Cosmetic Act (21 U.S.C. §301 et seq.), colors may include those exempt from certification colors (sometimes referred to as natural even though they can be synthetically manufactured) and certified colors (sometimes referred to as artificial), and a combination comprising any of the foregoing. In some embodiments, exemplary colors exempt from certification or natural colors may include, for example, annatto extract, (E160b), bixin, norbixin, astaxanthin, dehydrated beets (beet powder), beetroot red/betanin (E162), ultramarine blue, canthaxanthin (E161g), cryptoxanthin (E161c), rubixanthin (E161d), violanxanthin (E161e), rhodoxanthin (E161f), caramel (E150(a-d)), β-apo-8'-carotenal (E160e), β-carotene (E160a), alpha carotene, gamma carotene, ethyl ester of beta-apo-8 carotenal (E160f), flavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haematococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), and a combination comprising any of the foregoing.

In some embodiments, exemplary certified colors may include FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminum (E173), silver (E174), gold (E175), pigment rubine/lithol rubine BK (E180), calcium carbonate (E170), carbon black (E153), black PN/brilliant black BN (E151), green S/acid brilliant green BS (E142), and a combination comprising any of the foregoing. In some embodiments, certified colors may include FD&C aluminum lakes, which consist of the aluminum salts of FD&C dyes extended on an insoluble substrate of alumina hydrate. Additionally, in some embodiments, certified colors may be included as calcium salts.

In some embodiments, a consumable composition may include additional preservatives to provide freshness and to prevent the unwanted growth of bacteria, molds, fungi, or yeast. The addition of a preservative, including antioxidants, may also be used to maintain the composition's color, flavor, or texture. Exemplary preservatives may include benzoic acid alkali metal salts (e.g., sodium benzoate), sorbic acid alkali metal salts (e.g., potassium sorbate), ascorbic acid (Vitamin C), citric acid, calcium propionate, sodium erythorbate, sodium nitrite, calcium sorbate, butylated hydroxyanisole (BHA), butylated hydroxytoluene (BHT), ethylenediaminetetraacetic acid (EDTA), tocopherols (Vitamin E), straight chain polyphosphates, and a combination comprising any of the foregoing preservatives.

EXAMPLES

Example 1

A stable beverage emulsion including beta-carotene was made to include the ingredients as listed in Table 1.

TABLE 1

| Ingredient | Amount (Weight percentage) |
| --- | --- |
| Q-Naturale | 57 |
| Beta-carotene (30% solution) | 9.9 |
| d-limonene (95%) with other orange terpenes | 31.6 |
| Sodium benzoate | 0.25 |
| Citric Acid | 0.2 |
| Vitamin E | 1.0 |

In the emulsion of Example 1, an about 30% solution of beta-carotene suspended in carrier oil was used. The beta-carotene suspension included micronized crystals that remain stable in the carrier oil which in this example comprises corn oil. An amount of beta-carotene to provide about 9.9 percentage by weight in the final emulsion was added to an amount of d-limonene solvent to form a vitamin solution. The limonene selected for use was obtained from orange citrus extract and was purified to a level of purity of greater than about 95%; the remaining proportion of which includes various orange terpenes. Sodium benzoate, citric acid, and vitamin E in the amounts specified above were further added to the vitamin solution.

The vitamin solution was heated to about 127° C. and maintained at that temperature for a period of time of about 5 minutes. Analysis of the heated solution verified that crystals of beta-carotene were substantially dissolved in the heated vitamin solution. In this example, a portion of the vitamin solution was removed from the bulk solution and analyzed using light microscopy to verify that microcrystalline portions were substantially dissolved. The temperature of the vitamin solution was then decreased to a temperature of about 100° C.

An amount of Q-Naturale sufficient to provide about 57 weight percent of the Q-Naturale in the final prepared emulsion was then added to the vitamin solution to form a vitamin blend. The added Q-Naturale was held at a temperature of about 70° C. to about 90° C. The resulting composition was maintained at about that temperature for the remainder of the procedure. Following the addition of Q-Naturale, the composition was mixed for a period of several minutes in a high-shear mixer, and under conditions wherein only a minimum of foaming was present. In other examples, it has been found that processing the vitamin blend in a high-shear mixer may not be necessary to achieve suitable mixing.

To prepare the emulsion, the vitamin blend was homogenized using a commercially available two stage APV/Gaulin Homogenizer, manufactured by SPX Corporation (Charlotte, N.C.). The vitamin blend was processed by passing the blend through the two-stage homogenizer twice. For each pass, a first-stage pressure of about 6500 psi and a second-stage pressure of about 200 psi was applied.

Figure 3:
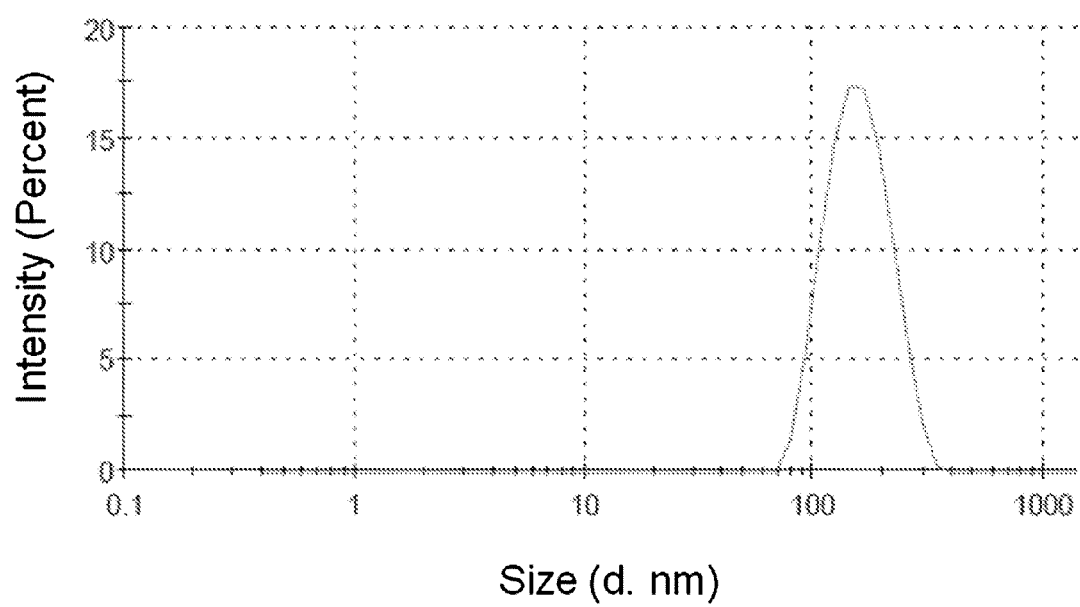
FIG. 3 is a graph showing the size of oil-phase regions in an emulsion.

The size of oil-phase regions of the resultant emulsion was measured using a commercially available dynamic light scattering system, Zetasizer™, manufactured by Malvern Instruments Ltd. (Worcestershire, U.K.). As further shown in FIG. 3, the size of oil-phase regions of the emulsion was found to range between about 0.1 micrometers and about 0.15 micrometers.

Example 2

The beverage emulsion of Example 1 was used in a reduced calorie orange flavored carbonated beverage product. The beverage product was prepared by addition of the emulsion at a level of about 0.07% by weight, and further included ingredients as listed in Table 2. Water used in the beverage samples was specifically purified prior to use by processes well known in the art such as filtration, distillation, or reverse osmosis.

TABLE 2

| Ingredient | Amount (Weight percentage) |
| --- | --- |
| Water | 98.54 |
| Medium Invert Sugar 76.5 brix | 0.66 |
| Erythritol | 0.06 |
| Stevia Leaf Extract | 0.06 |
| Citic Acid, Anhydrous | 0.05 |
| Sodium Benzoate | 0.03 |
| Malic Acid | 0.01 |

Additional amounts of minor ingredients, including apple and orange fruit juices from concentrate, were also provided in the beverage of Example 2. A group of samples of the beverage product was tested for stability towards light. The samples were placed in a light box for a time of 5 days and exposed to white light at an intensity of about 16,000 lux. The radiant energy provided to the samples over this period is greater than the energy that a sample may typically be exposed to during distribution stages of a product's lifetime. A second group of samples of the beverage product was tested for stability towards heat. The samples were heated to a temperature of about 120° F. for a period of 15 days. The thermal energy provided to the samples over this period is greater than the thermal energy that a sample may typically be exposed to during distribution stages of a product's lifetime. Each group was monitored over a period of at least six months and no noticeable change in color intensity or color purity was observed for either the heat-treated or light-treated group. In addition, no sedimentation was found in any of the beverage samples. For example, beverage ringing was not observed in any of the heat treated or light treated samples.

While many examples in this description refer to emulsions and beverages thereof, it is understood that those emulsions and beverages are described in an exemplary manner only and that other compositions and methods may be used. For example, any feature described for one embodiment may be used in any other embodiment. Additionally, other ingredients may be used, depending on the particular needs. Although the foregoing specific details describe certain embodiments, persons of ordinary skill in the art will recognize that various changes may be made in the details of these embodiments without departing from the spirit and scope of this invention as defined in the appended claims and other claims to be drawn to this invention, considering the doctrine of equivalents. Therefore, it should be understood that this invention is not limited to the specific details shown and described herein.

What is claimed is:

1. An oil-in-water emulsion comprising:
    an oil phase wherein the primary oil among all oils in said oil phase is a limonene oil which is extracted from citrus fruit rind; wherein up to about 30% by weight of all oils in said oil phase are carrier oils; vitamin A in an amount between about 1% and about 5% by weight; and quillaja extract in an amount between about 35% to about 65% by weight;
    water of no more than 50% by weight,
    and wherein said limonene oil includes less than about 5% of other terpene components other than said limonene oil and wherein said oil phase comprises particles with an average size of about 0.1 microns to about 0.5 microns.

2. The oil-in-water emulsion of claim 1 wherein said oil phase comprises particles with an average size of about 0.1 microns to about 0.2 microns.

3. The oil-in-water emulsion of claim 1 wherein said quillaja extract is in an amount between about 50% to about 60% by weight.

4. The oil-in-water emulsion of claim 1 further comprising vitamin E in an amount of about 0.1% to about 5% by weight.

5. The oil-in-water emulsion of claim 1 further comprising vitamin E in an amount of about 0.5% to about 2% by weight.

* * * * *